(12) United States Patent
Gilbert

(10) Patent No.: US 9,498,276 B2
(45) Date of Patent: Nov. 22, 2016

(54) SYSTEMS AND METHODS FOR NARROWBAND REAL IMPEDANCE CONTROL IN ELECTROSURGERY

(71) Applicant: COVIDIEN LP, Mansfield, MA (US)

(72) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 329 days.

(21) Appl. No.: 14/100,113

(22) Filed: Dec. 9, 2013

(65) Prior Publication Data

US 2014/0276750 A1 Sep. 18, 2014

Related U.S. Application Data

(60) Provisional application No. 61/794,191, filed on Mar. 15, 2013.

(51) Int. Cl.
*A61B 18/12* (2006.01)
*A61B 18/18* (2006.01)
*A61B 18/00* (2006.01)

(52) U.S. Cl.
CPC ....... *A61B 18/1233* (2013.01); *A61B 18/1206* (2013.01); *A61B 18/18* (2013.01);
(Continued)

(58) Field of Classification Search
CPC ................................ A61B 2018/00875; A61B 2018/00577; A61B 2018/00702;
(Continued)

(56) References Cited

U.S. PATENT DOCUMENTS

| 5,749,869 A | 5/1998 | Lindenmeier et al. |
| 6,200,314 B1 * | 3/2001 | Sherman ............ A61B 18/1206 606/34 |

(Continued)

FOREIGN PATENT DOCUMENTS

| DE | 179607 C | 3/1905 |
| DE | 390937 C | 3/1924 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Michael Peffley

(57) ABSTRACT

The electrosurgical systems and associated methods of the present disclosure perform narrowband real impedance control for precise treatment of tissue in electrosurgery. The electrosurgical systems include an electrosurgical generator that includes an output stage configured to generate electrosurgical energy to treat tissue, a plurality of sensors configured to sense voltage and current waveforms of the electrosurgical energy, and a controller coupled to the output stage to control the generated electrosurgical energy. The controller includes a signal processor that (1) determines a complex-valued voltage and a complex-valued current based on the voltage waveform and the current waveform sensed by the plurality of sensors using a plurality narrowband filters, and (2) calculates a real part of an impedance of the tissue using the complex-valued voltage and the complex-valued current. The controller also includes an output controller that controls the output stage based on the calculated real part of the impedance of the tissue.

19 Claims, 13 Drawing Sheets

(52) U.S. Cl.
CPC ............... *A61B 2018/00642* (2013.01); *A61B 2018/00702* (2013.01); *A61B 2018/00827* (2013.01); *A61B 2018/00875* (2013.01); *A61B 2018/00892* (2013.01)

(58) Field of Classification Search
CPC ............ A61B 2018/0072; A61B 2018/00732; A61B 2018/00767; A61B 18/1233
See application file for complete search history.

(56) References Cited

U.S. PATENT DOCUMENTS

| | | | |
|---|---|---|---|
| D574,323 S | 8/2008 | Waaler | |
| 8,162,932 B2* | 4/2012 | Podhajsky | A61B 18/1206 606/34 |
| 2005/0113819 A1 | 5/2005 | Wham et al. | |
| 2006/0155270 A1 | 7/2006 | Hancock et al. | |
| 2006/0224152 A1* | 10/2006 | Behnke | A61B 18/1206 606/34 |
| 2008/0234574 A1 | 9/2008 | Hancock et al. | |
| 2010/0217259 A1 | 8/2010 | Strauss | |
| 2010/0286686 A1 | 11/2010 | Hancock | |
| 2011/0071521 A1* | 3/2011 | Gilbert | H03H 17/0275 606/42 |
| 2011/0118727 A1 | 5/2011 | Fish et al. | |
| 2013/0035679 A1 | 2/2013 | Orszulak | |
| 2013/0053840 A1 | 2/2013 | Krapohl et al. | |
| 2013/0066311 A1 | 3/2013 | Smith et al. | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079673 A1 | 3/2013 | Stein et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1* | 8/2013 | Heckel | A61B 18/1206 703/2 |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0345696 A1 | 12/2013 | Behnke, II et al. | |
| 2014/0002056 A1 | 1/2014 | Moul et al. | |
| 2014/0015535 A1 | 1/2014 | Lopez | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2085044 A1 | 8/2009 |
| EP | 2301462 A1 | 3/2011 |
| EP | 2301463 A1 | 3/2011 |
| EP | 2510894 A1 | 10/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 2005/115235 A1 | 12/2005 |
| WO | 2006/050888 A1 | 5/2006 |
| WO | 2008/053532 A1 | 5/2008 |
| WO | 2012/076844 A1 | 6/2012 |
| WO | 2012110996 A2 | 8/2012 |

OTHER PUBLICATIONS

Vallfors et al., "Automatically Controlled Bipolar Electrosoagulation—'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

(56) References Cited

OTHER PUBLICATIONS

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedance", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight And Absorbance Imaging Of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 10/761,524, filed Jan. 21, 2004 inventor: Wham.
U.S. Appl. No. 11/242,458, filed Oct. 3, 2005 inventor: Becker.
U.S. Appl. No. 13/943,518, filed Jul. 16, 2013 inventor: Orszulak et al.
U.S. Appl. No. 14/069,534, filed Nov. 1, 2013 inventor: Digmann.
U.S. Appl. No. 14/096,341, filed Dec. 4, 2013 inventor: Johnson.
U.S. Appl. No. 14/098,859, filed Dec. 6, 2013 inventor: Johnson.
U.S. Appl. No. 14/100,113, filed Dec. 9, 2013 inventor: Gilbert.
U.S. Appl. No. 14/147,294, filed Jan. 3, 2014 inventor: Gilbert.
U.S. Appl. No. 14/147,312, filed Jan. 3, 2014 inventor: Gilbert.
U.S. Appl. No. 14/174,551, filed Feb. 6, 2014 inventor: Johnson.
U.S. Appl. No. 14/174,607, filed Feb. 6, 2014 inventor: Friedrichs.
U.S. Appl. No. 14/179,724, filed Feb. 13, 2014 inventor: Johnson.
U.S. Appl. No. 14/180,965, filed Feb. 14, 2014 inventor: Larson.
U.S. Appl. No. 14/181,114, filed Feb. 14, 2014 inventor: Larson.
U.S. Appl. No. 14/182,797, filed Feb. 18, 2014 inventor: Wham.
U.S. Appl. No. 14/183,196, filed Feb. 18, 2014 inventor: Krapohl.
U.S. Appl. No. 14/190,830, filed Feb. 26, 2014 inventor: Johnson.
U.S. Appl. No. 14/190,895, filed Feb. 26, 2014 inventor: Gilbert.
U.S. Appl. No. 14/192,112 dated Feb. 27, 2014 inventor: Weinberg.
U.S. Appl. No. 14/255,051 dated Apr. 17, 2014 inventor: Coulson.
European Search Report dated Oct. 23, 2014 and issued in corresponding EP Application No. 14156762.8.

* cited by examiner

SYSTEMS AND METHODS FOR NARROWBAND REAL IMPEDANCE CONTROL IN ELECTROSURGERY

CROSS REFERENCE TO RELATED APPLICATION

The present application claims the benefit of and priority to U.S. Provisional Application Ser. No. 61/794,191, filed on Mar. 15, 2013, the entire contents of which are incorporated herein by reference.

BACKGROUND

1. Technical Field

The present disclosure relates to electrosurgery. More particularly, the present disclosure relates to systems and methods for narrowband real impedance control for precise treatment of tissue in electrosurgery.

2. Background of Related Art

Electrosurgery involves the application of high-frequency electric current to cut or modify biological tissue during an electrosurgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The AC typically has a frequency above 100 kilohertz (kHz) to avoid muscle and/or nerve stimulation.

During electrosurgery, the AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the electrosurgical instrument itself. In monopolar electrosurgery, the return electrode is part of a device usually referred to as a return pad.

Some electrosurgical generators include a controller that controls the power delivered to the tissue over some period of time based upon measurements of the voltage and current near the output of the electrosurgical generator. These generators use a discrete Fourier transform (DFT) or polyphase demodulation to calculate the phase difference between measurements of the voltage and current for calculating real power and for performing calibration and compensation.

Some electrosurgical generators also calculate tissue impedance by dividing a wideband root mean square (RMS) voltage by a wideband RMS current under the assumption that the tissue is mostly resistive. Calibration and compensation techniques are employed to compensate for any gain- or phase-induced errors. However, noise in the wideband measurements of the RMS voltage and current is not attenuated. In fact, the "squaring" portion of the RMS calculations correlates the noise and adds the magnitude of the noise to the magnitudes of the RMS voltage and current. At low voltages and currents, the magnitude of the noise is even more significant with respect to the magnitudes of the RMS voltage and current, leading to inaccurate measurements of the RMS voltage and current.

SUMMARY

The systems and methods of the present disclosure provide accurate measurements of the RMS voltage and current, the tissue impedance, and the output power. In one aspect, the present disclosure features and an electrosurgical generator including an output stage, sensors, and a controller. The output stage generates electrosurgical energy to treat tissue and the sense a voltage waveform and a current waveform of the electrosurgical energy. The controller is coupled to the output stage and the sensors and controls the generated electrosurgical energy. The controller includes a signal processor that (1) determines a complex-valued voltage and a complex-valued current based on the voltage waveform and the current waveform sensed by the sensors using narrowband filters, and (2) calculates a real part of an impedance of the tissue using the complex-valued voltage and the complex-valued current. The controller also includes an output controller that controls the output stage based on the calculated real part of the impedance of the tissue.

The narrowband filters may be polyphase decimator filters or Goertzel DFT filters. The polyphase decimator filters may be heterodyned carrier-centered polyphase filters having a center frequency that is a harmonic multiple of a frequency of the electrosurgical energy. Also, the electrosurgical energy may be Radio Frequency (RF) energy.

In aspects, the signal processor calculates the real part of the tissue impedance according to the following equation:

$$\frac{ac+bd}{c^2+d^2},$$

where a is the real part of the complex-valued voltage, b is the imaginary part of the complex-valued voltage, c is the real part of the complex-valued current, and d is the imaginary part of the complex-valued current. The signal processor may also calculate the imaginary part of the tissue impedance according to the following equation:

$$\frac{bc-ad}{c^2+d^2},$$

where a is the real part of the complex-valued voltage, b is the imaginary part of the complex-valued voltage, c is the real part of the complex-valued current, and d is the imaginary part of the complex-valued current.

In aspects, the signal processor may calculate the magnitude of the tissue impedance based on the calculated real and imaginary parts of the tissue impedance.

In aspects, the electrosurgical generator may include analog-to-digital converters (ADCs) that sample the sensed voltage waveform and the sensed current waveform to obtain a predetermined number of samples of each of the sensed voltage waveform and the sensed current waveform. The predetermined number of samples may correspond to an integer number of periods of the voltage waveform and the current waveform. The electrosurgical generator may also include lowpass filters that filter the sensed voltage waveform and the sensed current waveform before the ADCs sample the sensed voltage waveform and the sensed current waveform. The electrosurgical generator may also include decimators that decimate the sampled voltage waveform and the sampled current waveform before the narrowband filters filter the decimated voltage waveform and the decimated current waveform.

In aspects, the output controller generates a feedback waveform based on a difference between the real part of the impedance and a desired real part of the impedance. The feedback waveform may be used to control the output stage.

In aspects, the controller may be implemented in a field programmable gate array, an application specific integrated circuit, an application specific standard product integrated circuit, or a digital signal processor.

In another aspect, the present disclosure features a method for an electrosurgical generator. The method includes generating electrosurgical energy to treat tissue, sensing a voltage waveform and a current waveform of the generated electrosurgical energy, determining a complex-valued voltage and a complex-valued current based on the sensed voltage waveform and the sensed current waveform using narrowband filters, calculating a real part of an impedance of the tissue, and controlling the electrosurgical energy based on the calculated real part of the impedance of the tissue.

In aspects, the narrowband filters may be polyphase decimator filters or Goertzel DFT filters. The polyphase decimator filters may be heterodyned carrier-centered polyphase filters having a center frequency that is a harmonic multiple of a frequency of the electrosurgical energy.

In aspects, the method may further include calculating the real part of the tissue impedance according to the following equation:

$$\frac{ac + bd}{c^2 + d^2},$$

where a is the real part of the complex-valued voltage, b is the imaginary part of the complex-valued voltage, c is the real part of the complex-valued current, and d is the imaginary part of the complex-valued current. The method may also include calculating the imaginary part of the tissue impedance according to the following equation:

$$\frac{bc - ad}{c^2 + d^2},$$

where a is the real part of the complex-valued voltage, b is the imaginary part of the complex-valued voltage, c is the real part of the complex-valued current, and d is the imaginary part of the complex-valued current. The method may also include calculating the magnitude of the tissue impedance based on the calculated real and imaginary parts of the tissue impedance. The method may also include sampling the sensed voltage waveform and the sensed current waveform to obtain a predetermined number of samples of each of the sensed voltage waveform and the sensed current waveform, in which the predetermined number of samples corresponds to an integer number of periods of the voltage waveform and the current waveform.

In yet another aspect, the present disclosure features non-transitory storage medium storing instructions that, when executed by a processor, performs a method for an electrosurgical generator. The method includes generating electrosurgical energy to treat tissue, sensing a voltage waveform and a current waveform of the generated electrosurgical energy, determining a complex-valued voltage and a complex-valued current based on the sensed voltage waveform and the sensed current waveform using narrowband filters, calculating a real part of an impedance of the tissue, and controlling the electrosurgical energy based on the calculated real part of the impedance of the tissue.

In aspects, the processor may be a field programmable gate array (FPGA), an application specific integrated circuit (ASIC), a digital signal processor (DSP), a programmable digital signal processor, or any combination of these processors.

BRIEF DESCRIPTION OF THE DRAWINGS

Various embodiment of the present disclosure are described with reference to the accompanying drawings wherein.

DETAILED DESCRIPTION

The electrosurgical systems and methods according to the present disclosure control the delivery of energy to tissue based on calculations of the real part of the tissue impedance using narrowband signal processing coupled with wideband power control without relying on any detailed knowledge of the components disposed between the output of the generator and the tissue to be treated, e.g., cabling and instruments and relying upon known tissue characteristics within the narrowband. The narrowband signal processing may employ a single-frequency discrete Fourier transform (DFT), such as a Goertzel filter, or polyphase demodulation. Should detailed knowledge of the cabling components be known a priori, a simplified compensation technique may be applied at the tissue resistance extremes, if necessary.

Figure 1:
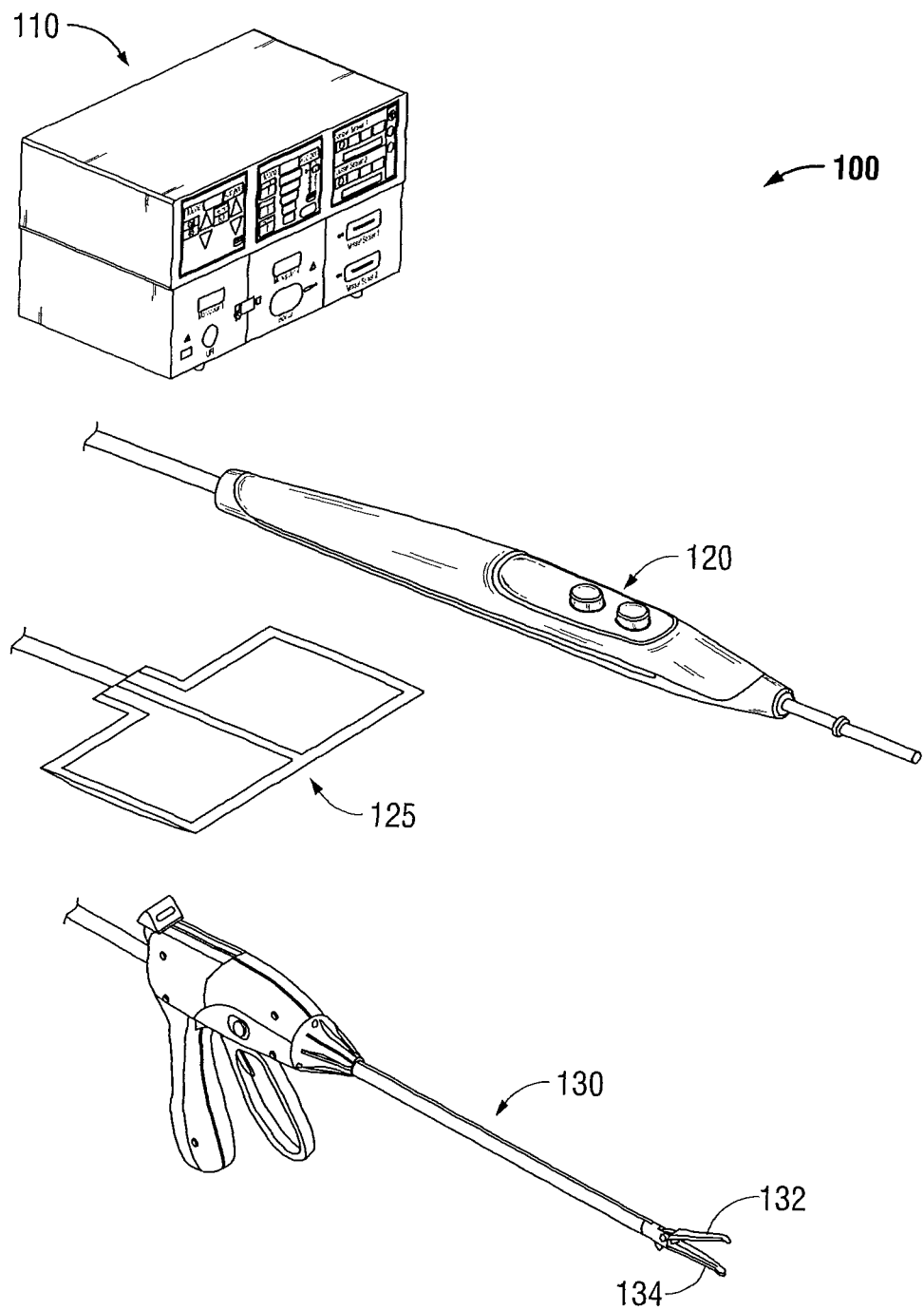
FIG. 1 is an illustration of an electrosurgical system including a generator in accordance with embodiments of the present disclosure.

FIG. 1 illustrates an electrosurgical system 100 in accordance with embodiments of the present disclosure. The electrosurgical system 100 includes an electrosurgical generator 110 which generates electrosurgical energy to treat tissue of a patient. The electrosurgical generator 110 generates an appropriate level of electrosurgical energy based on the selected mode of operation (e.g., cutting, coagulating, ablating, or sealing) and/or the sensed voltage and current waveforms of the electrosurgical energy. The electrosurgical system 100 may also include a plurality of output connectors corresponding to a variety of electrosurgical instruments.

The electrosurgical system 100 further includes a monopolar electrosurgical instrument 120 having an electrode for treating tissue of the patient (e.g., an electrosurgical cutting probe or ablation electrode) with a return pad 125. The monopolar electrosurgical instrument 120 can be connected to the electrosurgical generator 110 via one of the plurality of output connectors. The electrosurgical generator 110 may generate electrosurgical energy in the form of radio frequency (RF) energy. The electrosurgical energy is supplied to the monopolar electrosurgical instrument 120, which applies the electrosurgical energy to treat the tissue. The electrosurgical energy is returned to the electrosurgical generator 110 through the return pad 125. The return pad 125 provides a sufficient contact area with the patient's tissue so as to minimize the risk of tissue damage due to the electrosurgical energy applied to the tissue. In addition, the electrosurgical generator 110 and the return pad 125 may be configured to monitor tissue-to-patient contact to insure that sufficient contact exists between the return pad 125 and the patient to minimize the risk of tissue damages.

The electrosurgical system 100 also includes a bipolar electrosurgical instrument 130, which can be connected to the electrosurgical generator 110 via one of the plurality of output connectors. During operation of the bipolar electrosurgical instrument, electrosurgical energy is supplied to one of the two jaw members, e.g., jaw member 132, of the instrument's forceps, is applied to treat the tissue, and is returned to the electrosurgical generator 110 through the other jaw member, e.g., jaw member 134.

The electrosurgical generator 110 may be any suitable type of generator and may include a plurality of connectors to accommodate various types of electrosurgical instruments (e.g., monopolar electrosurgical instrument 120 and bipolar electrosurgical instrument 130). The electrosurgical generator 110 may also be configured to operate in a variety of modes, such as ablation, cutting, coagulation, and sealing. The electrosurgical generator 110 may include a switching mechanism (e.g., relays) to switch the supply of RF energy among the connectors to which various electrosurgical instruments may be connected. For example, when an electrosurgical instrument 120 is connected to the electrosurgical generator 110, the switching mechanism switches the supply of RF energy to the monopolar plug. In embodiments, the electrosurgical generator 110 may be configured to provide RF energy to a plurality of instruments simultaneously.

The electrosurgical generator 110 includes a user interface having suitable user controls (e.g., buttons, activators, switches, or touch screens) for providing control parameters to the electrosurgical generator 110. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 120 and 130 may also include a plurality of user controls. In addition, the electrosurgical generator 110 may include one or more display screens for displaying a variety of information related to operation of the electrosurgical generator 110 (e.g., intensity settings and treatment complete indicators). The electrosurgical instruments 120 and 130 may also include a plurality of input controls that may be redundant with certain input controls of the electrosurgical generator 110. Placing the input controls at the electrosurgical instruments 120 and 130 allows for easier and faster modification of the electrosurgical energy parameters during the surgical procedure without requiring interaction with the electrosurgical generator 110.

Figure 2A:
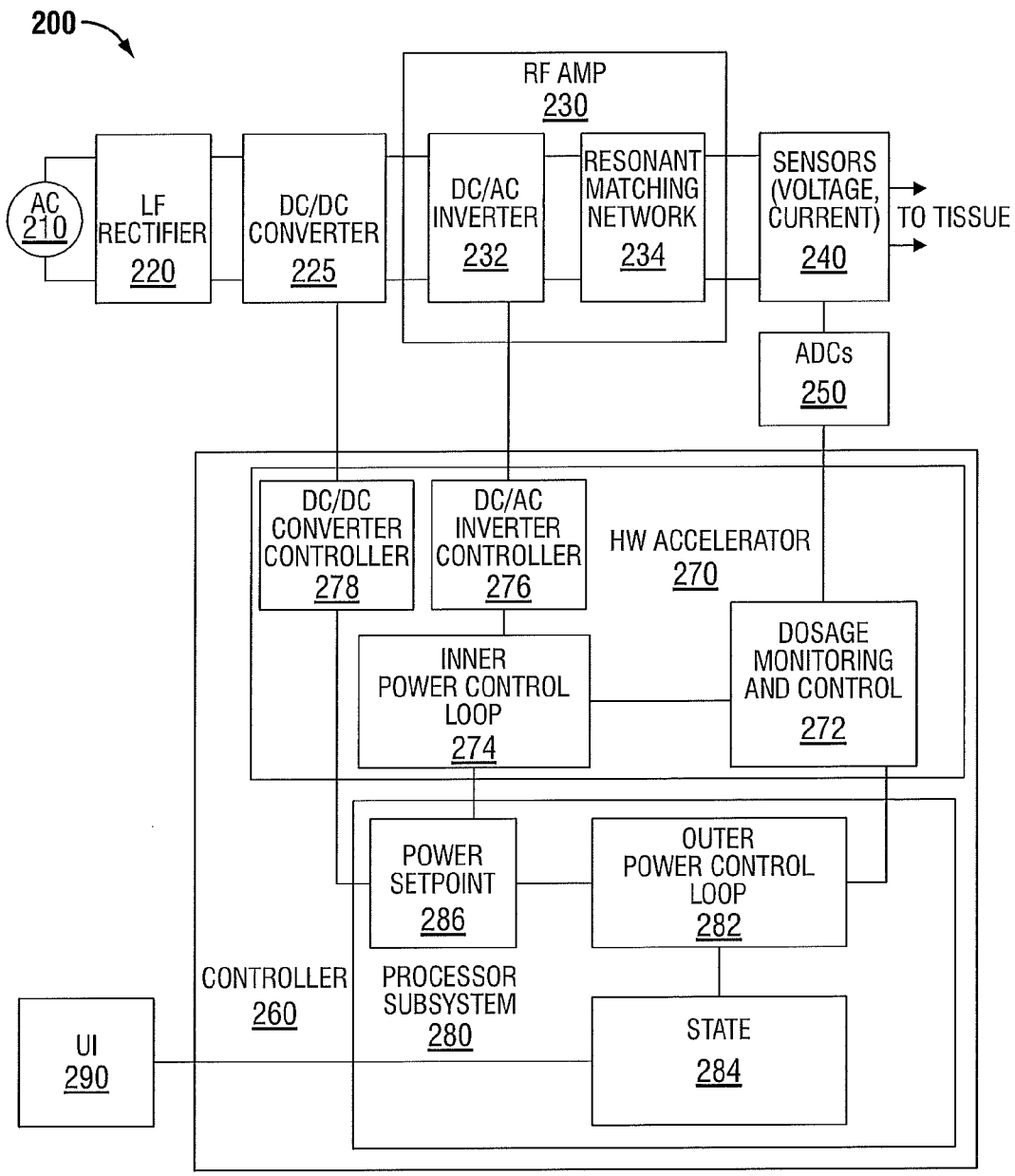
FIG. 2A is a block diagram of an electrosurgical system including generator circuitry according to a combination of a modified-Kahn technique and a Class S generator topology in accordance with one embodiment of the present disclosure.

FIG. 2A is a block diagram of generator circuitry 200 within the electrosurgical generator of FIG. 1. The generator circuitry 200 includes a low frequency (LF) rectifier 220, a direct current-to-direct current (DC/DC) converter 225, an RF amplifier 230, a plurality of sensors 240, analog-to-digital converters (ADCs) 250, a controller 260, a hardware accelerator 270, a processor subsystem 280, and a user interface (UI) 290. The generator circuitry 200 is configured to connect to a power source 210, such as a wall power outlet or other power outlet, which generates alternating current (AC) having a low frequency (e.g., 25 Hz, 50 Hz, or 60 Hz). The power source 210 provides the AC power to the LF rectifier 220, which converts the AC to direct current (DC). Alternatively, the power source 210 and the LF rectifier 220 may be replaced by a battery or other suitable device to provide DC power.

The DC output from the LF rectifier 220 is provided to the DC/DC converter 225 which converts the DC to a desired level. The converted DC is provided to the RF amplifier 230, which includes a DC-to-AC (DC/AC) inverter 232 and a resonant matching network 234. The DC/AC inverter 232 converts the converted DC to an AC waveform having a frequency suitable for an electrosurgical procedure (e.g., 472 kHz, 29.5 kHz, and 19.7 kHz).

The appropriate frequency for the electrosurgical energy may differ based on electrosurgical procedures and modes of electrosurgery. For example, nerve and muscle stimulations cease at about 100,000 cycles per second (100 kHz) above which point some electrosurgical procedures can be performed safely, i.e., the electrosurgical energy can pass through a patient to targeted tissue with minimal neuromuscular stimulation. For example, typically, ablation procedures use a frequency of 472 kHz. Other electrosurgical procedures can be performed at pulsed rates lower than 100 kHz, e.g., 29.5 kHz or 19.7 kHz, with minimal risk of damaging nerves and muscles, e.g., Fulgurate or Spray. The DC/AC inverter 232 can output AC signals with various frequencies suitable for electrosurgical operations.

As described above, the RF amplifier 230 includes a resonant matching network 234. The resonant matching network 234 is coupled to the output of the DC/AC inverter 232 to match the impedance at the DC/AC inverter 232 to the impedance of the tissue so that there is maximum or optimal power transfer between the generator circuitry 200 and the tissue.

Figure 2B:
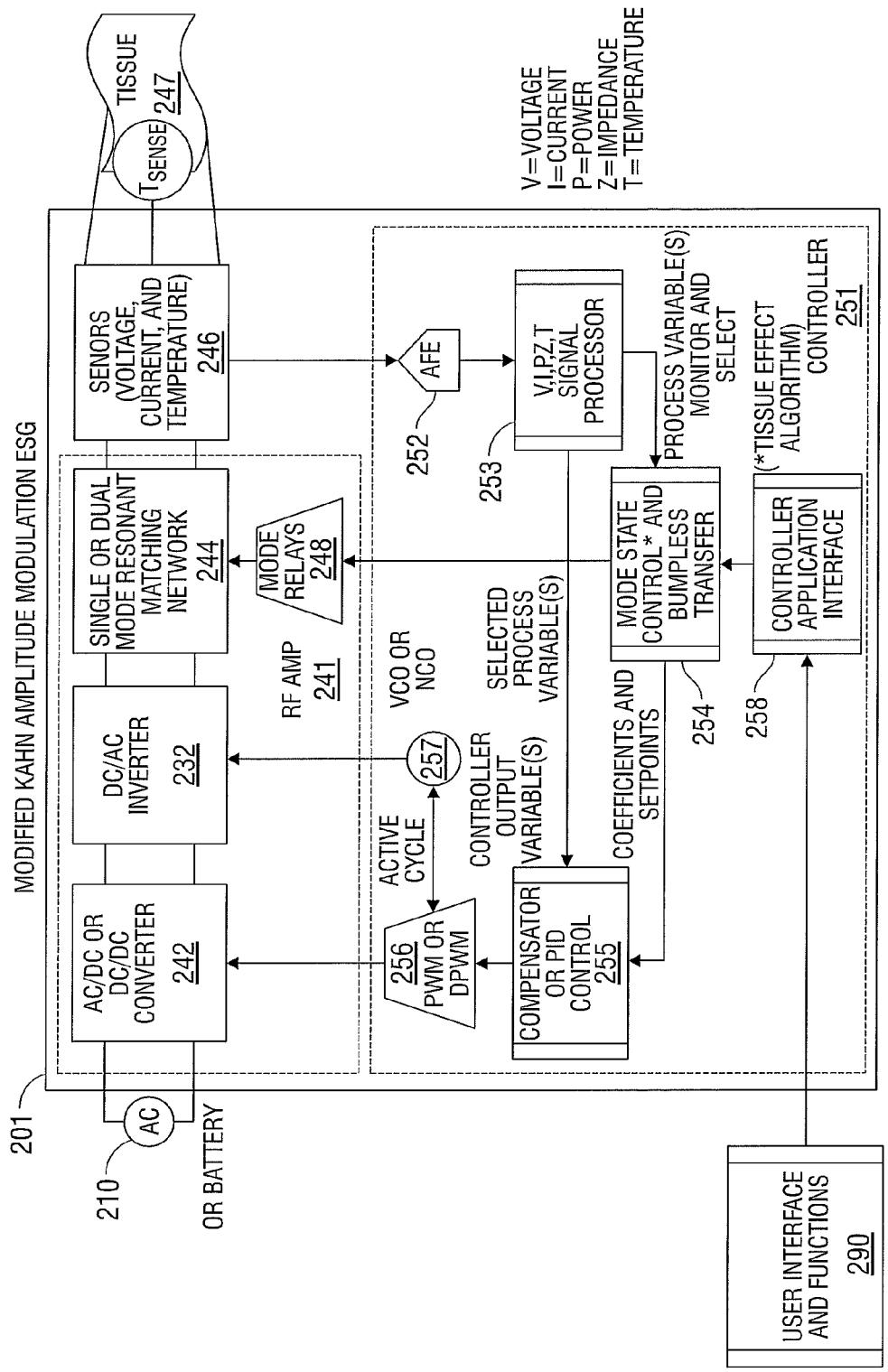
FIG. 2B is a block diagram of an electrosurgical system including generator circuitry according to the modified-Kahn technique in accordance with another embodiment of the present disclosure.
Figure 2C:
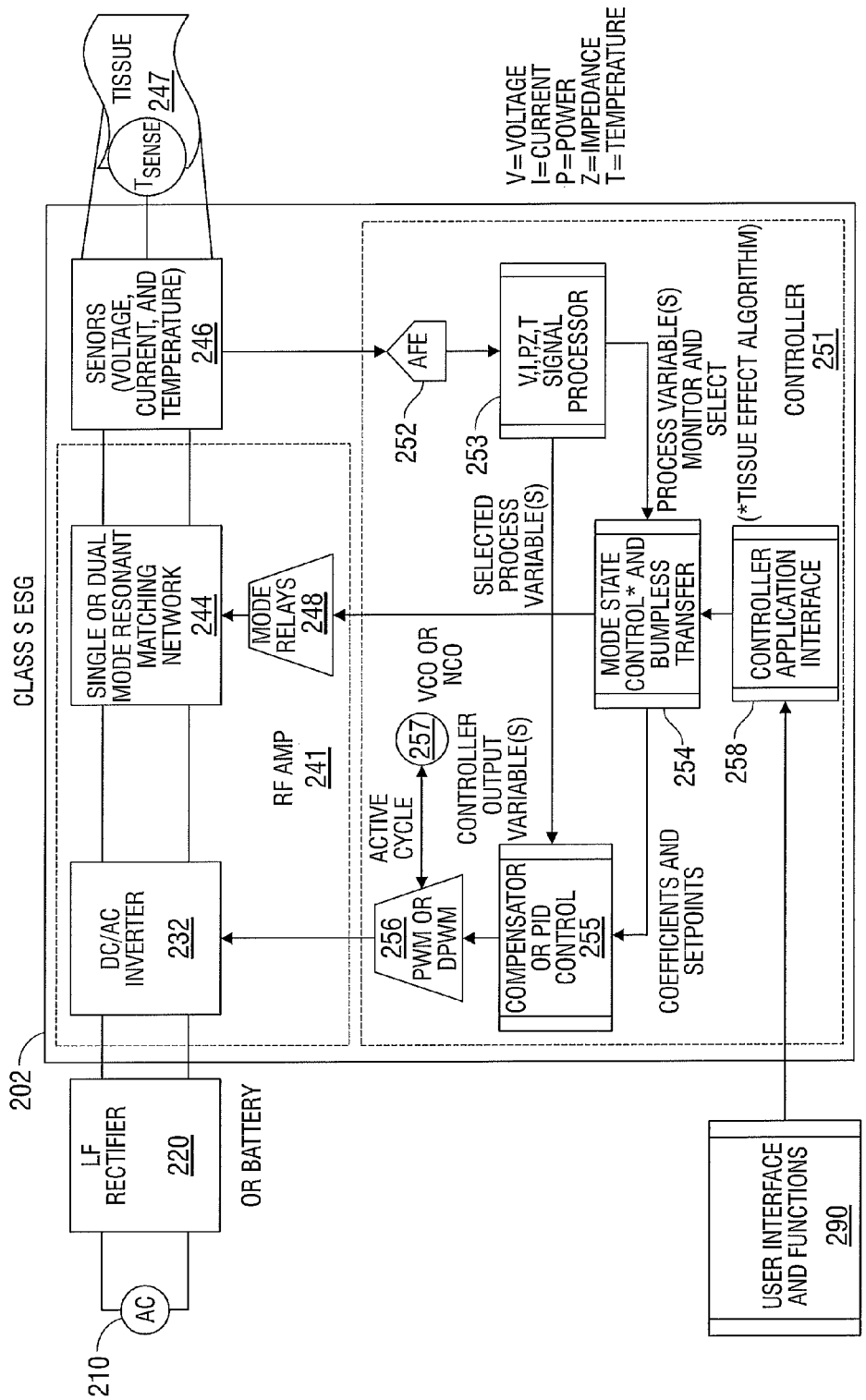
FIG. 2C is a block diagram of an electrosurgical system including generator circuitry according to the Class S device topology in accordance with still another embodiment of the present disclosure.

The electrosurgical energy provided by the DC/AC inverter 232 of the RF amplifier 230 is controlled by the controller 260. The voltage and current waveforms of the electrosurgical energy output from the DC/AC inverter 232 are sensed by the plurality of sensors 240 and provided to the controller 260, which generates control signals from a DC/DC converter controller 278, e.g., a pulse width modulator (PWM) or digital pulse width modulator (DPWM) to control the output of the DC/DC converter 225 and from a DC/AC inverter controller 276 to control the output of the DC/AC inverter 232. The controller 260 also receives input signals via the user interface (UI) 290. The UI 290 allows a user to select a type of electrosurgical procedure (e.g., monopolar or bipolar) and a mode (e.g., coagulation, ablation, sealing, or cutting), or input desired control parameters for the electrosurgical procedure or the mode. The DC/DC converter 225 of FIG. 2A may be fixed or variable depending on the power setting or desired surgical effects. When it is fixed, the RF amplifier behaves as a Class S device, which is shown in FIG. 2C. When it is variable, it behaves as a device according to the modified-Kahn technique, which is shown in FIG. 2B.

The plurality of sensors 240 sense voltage and current at the output of the RF amplifier 230. The plurality of sensors 240 may include two or more pairs or sets of voltage and current sensors that provide redundant measurements of the voltage and current. This redundancy ensures the reliability, accuracy, and stability of the voltage and current measurements at the output of the RF amplifier 230. In embodiments, the plurality of sensors 240 may include fewer or more sets of voltage and current sensors depending on the application or the design requirements. The plurality of sensors 240 may also measure the voltage and current output from other components of the generator circuitry 200 such as the DC/AC inverter 232 or the resonant matching network 234. The plurality of sensors 240 may include any known technology for measuring voltage and current including, for example, a Rogowski coil.

The sensed voltage and current waveforms are fed to analog-to-digital converters (ADCs) 250. The ADCs 250 sample the sensed voltage and current waveforms to obtain digital samples of the voltage and current waveforms. This is also often referred to as an Analog Front End (AFE). The digital samples of the voltage and current waveforms are processed by the controller 260 and used to generate control signals to control the DC/AC inverter 232 of the RF amplifier 230 and the DC/DC converter 225. The ADCs 250 may be configured to sample the sensed voltage and current waveforms at a sample frequency that is an integer multiple of the RF frequency.

As shown in the embodiment of FIG. 2A, the controller 260 includes a hardware accelerator 270 and a processor subsystem 280. As described above, the controller 260 is also coupled to a UI 290, which receives input commands from a user and displays output and input information related to characteristics of the electrosurgical energy (e.g., selected power level). The hardware accelerator 270 processes the output from the ADCs 250 and cooperates with the processor subsystem 280 to generate control signals.

The hardware accelerator 270 includes a dosage monitoring and control (DMAC) 272, an inner power control loop 274, a DC/AC inverter controller 276, and a DC/DC converter controller 278. All or a portion of the controller 260 may be implemented by a field programmable gate array (FPGA), an application specific integrated circuit (ASIC), a digital signal processor (DSP), and/or a microcontroller.

The DMAC 272 receives samples of the sensed voltage and current waveforms from the ADCs 250 and calculates the average real power and the real part of the tissue impedance, as described in greater detail below. The DMAC 272 then provides the real power and the real part of the impedance of the tissue to the inner power control loop 274, which generates a control signal for the DC/AC inverter controller 276 based on one or more of the real power and the real part of the impedance of the tissue. The DC/AC inverter controller 276 in turn generates a first pulse-width modulation (PWM) control signal to control the output of the DC/AC inverter 232.

The processor subsystem 280 includes an outer power control loop 282, a state machine 284, and a power setpoint circuit 286. The processor subsystem 280 generates a second PWM control signal based on the output of the DMAC 272 and parameters (e.g., electrosurgical mode) selected by the user via the UI 290. Specifically, the parameters selected by the user are provided to the state machine 284 which determines a state or mode of the generator circuitry 200. The outer power control loop 282 uses this state information and the output from the DMAC 272 to determine control data. The control data is provided to the power setpoint circuit 286 which generates a power setpoint based on the control data. The DC/DC converter controller 278 uses the power setpoint to generate an appropriate PWM control signal for controlling the DC/DC converter 225 to converter the DC output from the LF rectifier 220 to a desired level. If the user does not provide operational parameters to the state machine 284 via the UI 290, then the state machine 284 may maintain or enter a default state.

Figure 3:
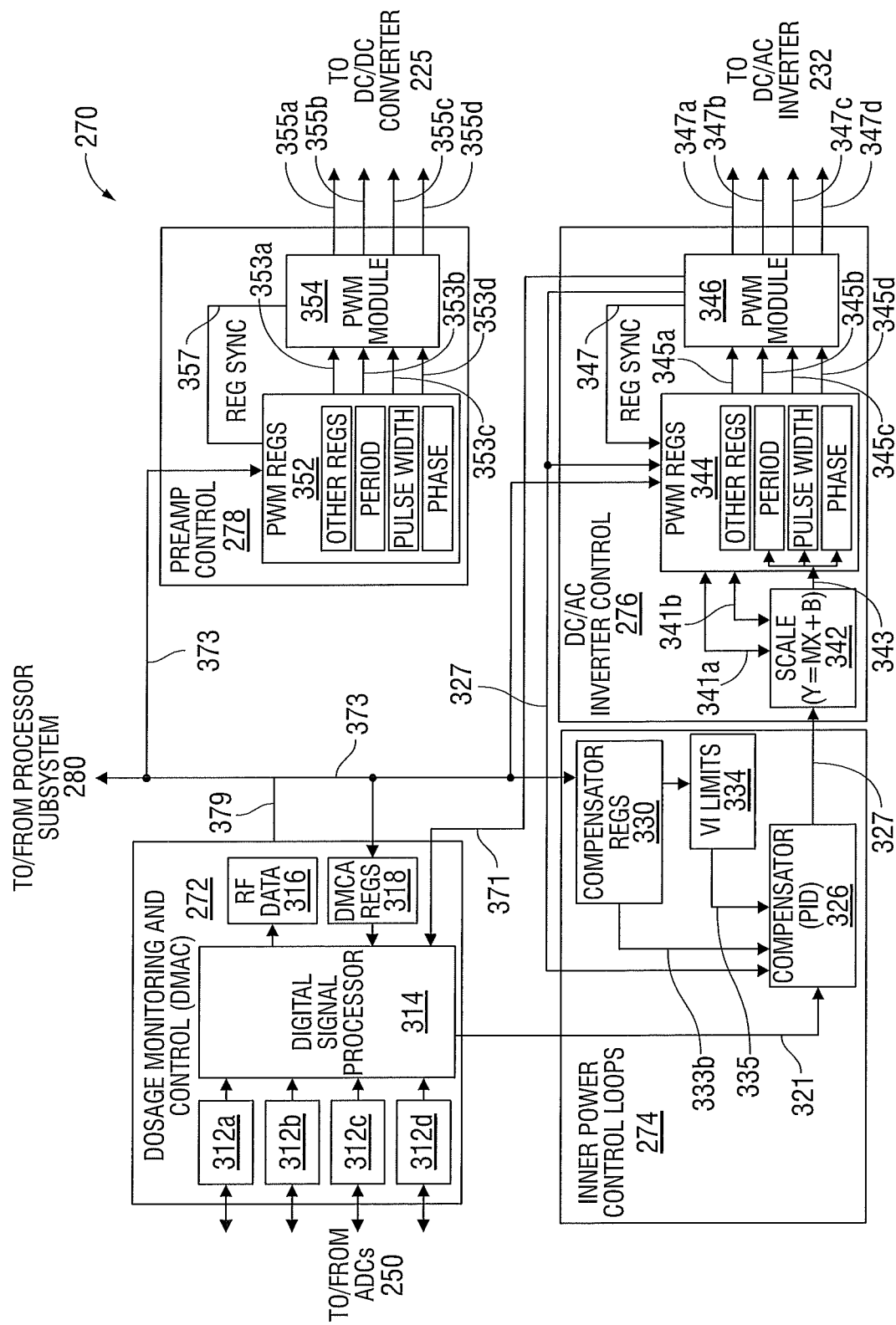
FIG. 3 is a schematic block diagram of a controller of the generator circuitry of FIG. 2A.

FIG. 3 shows a more detailed diagram of the hardware accelerator 270 of FIG. 2A. The hardware accelerator 270 implements those functions of the generator circuitry 200 that may have special processing requirements such as high processing speeds. The hardware accelerator 270 includes the DMAC 272, the inner power loop control 274, the DC/AC inverter controller 276, and the DC/DC converter controller 278 shown in FIG. 2A.

The DMAC 272 includes four analog-to-digital converter (ADC) controllers 312a-312d, a digital signal processor 314, an RF data registers 316, and DMAC registers 318. The ADC controllers 312a-312d control the operation of the ADCs 250 (FIG. 2), which convert sensed voltage and current waveforms into digital data. The digital data is then provided to the digital signal processor 314 that implements various filtering and other digital signal processing functions, some of which are described in more detail below.

The sensed voltage and current are the digital input to the ADCs 250, which sample the sensed voltage and current. The ADC controllers 312a-312d provide operational parameters, including a predetermined sampling rate, to the ADCs 250 so that the ADCs sample the sensed voltage and current synchronously at a predetermined sampling rate, i.e., a predetermined number of samples per second, or predetermined sampling period that is coherent with the RF inverter frequency, i.e., an integer multiple sampling frequency to the RF inverter frequency. The ADC controllers 312a-312d control the operation of the ADCs 250, which convert sensed voltage and current waveforms into digital data. The digital data is then provided to the digital signal processor 314 that implements various filtering and other digital signal processing functions, some of which are described in more detail below.

The sensed voltage and current are input to the ADCs 250, which sample the sensed voltage and current. The ADC controllers 312a-312d provide operational parameters, including a predetermined sampling rate, to the ADCs 250 so that the ADCs sample the sensed voltage and current synchronously at a predetermined sampling rate, i.e., a predetermined number of samples per second, or predetermined sampling period. The ADC controllers 312a-312d may be configured to control the ADCs 250 so that the sampling period corresponds to an integer multiple of the RF frequency of the voltage and current waveforms. This is often referred to as coherent sampling.

The digital data obtained by sampling the voltage and current waveforms is provided to the digital signal processor 314 via the ADC controllers 312a-312d. The digital signal processor 314 uses the digital data to calculate a complex voltage $V_{comp}$, a complex current $I_{comp}$, a real power $P_{real}$, and a real part of the tissue impedance $Z_{real}$. Generally, tissue impedance is real or resistive, but can have a small capacitive component after the tissue is "cooked." Further, a cable between the electrosurgical generator and the tissue also has resistive and reactive components. For these reasons, electrosurgical generators typically include controls systems that compensate for these parasitics to more accurately measure the tissue impedance. These control systems, however, require complex computations that are computationally inefficient, which results in additional cost to perform the tissue impedance calculations in a timely manner or at update rates commensurate to the capabilities of the RF control loop calculations.

In alternative embodiments depicted in FIGS. 2A and 2B, the hardware accelerator is not available and many of the primary RF measurement and control functions just described reside instead entirely within a programmable device called an application specific standard product (ASSP) integrated circuit that includes at least a DSP core processor and multiple digital pulse width modulators (DPWM) that are substantially similar in function to the hardware accelerator and its DSP and/or microcontroller core.

In other embodiments, there may also be a second microprocessor core available within the ASSP that contains additional ADCs which may be connected to the sensors for performing the redundant dosage monitoring functions separately from the RF control functions. The second processor may also perform user interface functions such as receiving and requesting power settings, activation requests, and so forth for the user from the RF controller. The ASSP may also utilize only one RF control loop (or compensator loop), instead of two "inner" and "outer" compensator loops, for controlling directly any of the following: power, voltage, current, temperature, or impedance. This loop may use a single proportional-integral-derivative compensator that changes between these process variables using bumpless transfer methods and saturable limits.

FIG. 2B shows an electrosurgical system including generator circuitry according to the modified-Kahn technique 201. The generator circuitry 201 includes an RF amplifier 241 and a controller 251 for controlling the RF amplifier 241 to deliver electrosurgical energy having desired characteristics to tissue 247 being treated. The RF amplifier 241 receives AC or DC from the power source 210. The RF amplifier includes an AC/DC or DC/DC converter 242, which converts the AC or DC provided by the power source 210 into a suitable level of DC. As in FIG. 2A, the RF amplifier 241 also includes a DC/AC inverter 232 which converts the DC to AC. The RF amplifier 241 also includes a single- or dual-mode resonant matching network 244 and mode relays 248 for switching modes of the resonant matching network 244.

The output from the RF amplifier 241 is provided to sensors 246, which may include voltage sensors, current sensors, and temperature sensors. The sensor signals output from sensors 246 are provided to the controller 251 via an analog front end (AFE) 252 of the controller 251. The AFE conditions and samples the sensor signals to obtain digital sensor data representing the sensor signals. The controller 251 also includes a signal processor 253, a mode state control and bumpless transfer unit 254, a compensator or PID controller 255, a pulse width modulator (PWM) or digital pulse width modulator (DPWM) 256, and a voltage-controlled oscillator or numerically-controlled oscillator 257.

The signal processor 253 receives the digital sensor data and performs the calculations and other functions of the systems and methods according to the present disclosure. Among other things, the signal processor 253 calculates the real and imaginary parts of the sensed voltage and current, the impedance, and/or the power, and performs functions to control one or more of the voltage, current, power, impedance, and temperature. The signal processor 253 also generates and provides process variables to the mode state control and bumpless transfer unit 254 and a compensator or PID controller 255. The mode state control and bumpless transfer unit 254 controls the mode relays 248 for the single or dual mode resonant matching network 244 according to the tissue effect algorithm, and generates and provides coefficients and setpoints to the compensator or PID controller 255.

The compensator or PID controller 255 generates controller output variables and provides them to the pulse width modulator (PWM) or digital pulse width modulator (DPWM) 256. The pulse width modulator (PWM) or digital pulse width modulator (DPWM) 256 receives an oscillator signal from the voltage-controlled oscillator or the numerically-controlled oscillator 257 and generates a control signal for controlling the AC/DC or DC/DC converter 242. The voltage-controlled oscillator or the numerically-controlled oscillator 257 also generates control signals for controlling the DC/AC inverter 232.

Like the generator circuitry 200 of FIG. 2A, the generator circuitry 201 includes a user interface 201 through which a user can control and/or monitor the functions of the generator circuitry 201 via a controller application interface 258 of the controller 251.

FIG. 2C shows an electrosurgical system including generator circuitry according to a Class S device topology 202. Unlike the generator circuitry 201 of FIG. 2B, the generator circuitry 202 does not include the AC/DC or DC/DC Converter 242. An external low-frequency (LF) rectifier 220 or battery provides an appropriate level of DC to the DC/AC Inverter 232 of the RF amplifier 241. As shown in FIG. 2C, the PWM or DPWM 256 receives an oscillator signal from the VCO or NCO 257 and generates a control signal for controlling the DC/AC Inverter 232.

The present disclosure relates to the resistive component of the impedance of the tissue because the resistive component (i.e., the real part of the impedance) is where the majority of power is dissipated in the tissue and the real part of the components between the electrosurgical generator and the tissue is (or should be by design) only a few percent of the real part of the tissue impedance. Also, it is assumed that the tissue resistance is roughly constant throughout the frequencies of interest in electrosurgery, i.e., from 100 kHz to 10 MHz. Thus, assuming that most power is dissipated in the tissue, calculating only the real part of the tissue impedance would increase computational efficiency.

The output of the digital signal processor 314 is provided to the processor subsystem 280 of FIG. 2A via RF data registers 316. The DMAC 272 also includes DMAC registers 318 that receive and store relevant parameters for the digital signal processor 314. The digital signal processor 314 further receives signals from a PWM module 346 of the DC/AC inverter controller 276.

The DMAC 272 provides a control signal to the inner power control loop 274 via signal line 321 and to the processor subsystem 280 via signal line 379. The inner power control loop 274 processes the control signal and outputs a control signal to the DC/AC inverter controller 276. The inner power control loop 274 includes a compensator 326, compensator registers 330, and VI limiter 334. The signal line 321 carries and provides a real part of the impedance to the compensator 326.

When there is a user input, the processor subsystem 280 receives the user input and processes it with the outputs from the digital signal processor 314 via a signal line 379. The processor subsystem 280 provides control signals via a compensator registers 330 to a VI limiter 334, which corresponds to the power setpoint circuit 286 in FIG. 2A. The VI limiter 334 then provides a desired power profile (e.g., a minimum and a maximum limits of the power for a set electrosurgical mode or operation) based on the user input and the output of the digital signal processor 314, the compensator registers 330 also provide other control parameters to the compensator 326, and then the compensator 326 combines all control parameters from the compensator registers 330, the VI limiter 334, the multiplexer 324, and the impedance gain 322 to generate output to the DC/AC inverter controller 276 via signal line 327.

The DC/AC inverter controller 276 receives a control parameter and outputs control signals that drives the DC/AC inverter 232. The DC/AC inverter controller 276 includes a scale unit 342, PWM registers 344, and the PWM module 346. The scale unit 342 scales the output of the compensator registers 330 by multiplying and/or adding a number to the output. The scale unit 342 receives a number for multiplication and/or a number for addition from the PWM registers 344 via signal lines, 341a and 341b. The PWM registers 344 store several relevant parameters to control the DC/AC inverter 232, e.g., a period, a pulse width, and a phase of the AC signal to be generated by the DC/AC inverter 232 and other related parameters. The PWM module 346 receives output from the PWM registers 344 and generates four control signals, 347a-347d, that control four transistors of the DC/AC inverter 232 of the RF amplifier 230 in FIG. 2A. The PWM module 346 also synchronizes its information with the information in the PWM registers 344 via a register sync signal 347.

The PWM module 346 further provides control signals to the compensator 326 of the inner power control loop 274. The processor subsystem 280 provides control signals to the PWM module 346. In this way, the DC/AC inverter controller 276 can control the DC/AC inverter 232 of the RF amplifier 230 with integrated internal input (i.e., processed results from the plurality of sensors by the DMAC 272) and external input (i.e., processed results from the user input by the processor subsystem 280).

The processor subsystem 280 also sends the control signals to the DC/DC converter controller 278 via signal line 373. The DC/DC converter controller 278 processes the control signals and generates another control signals so that the DC/DC converter 225 converts direct current to a desired level suitable for being converted by the RF amplifier 230. The DC/DC converter controller 278 includes PWM registers 352 and a PWM module 354. The PWM registers 352 receive outputs from the processor subsystem 280 via signal line 373 and stores relevant parameters as the PWM registers 344 does. The PWM module 354 also sends a register sync signal to the PWM registers 352 and generates four control signals, 355a-355d, that control four transistors of the DC/DC converter 225 in FIG. 2A.

Figure 4:
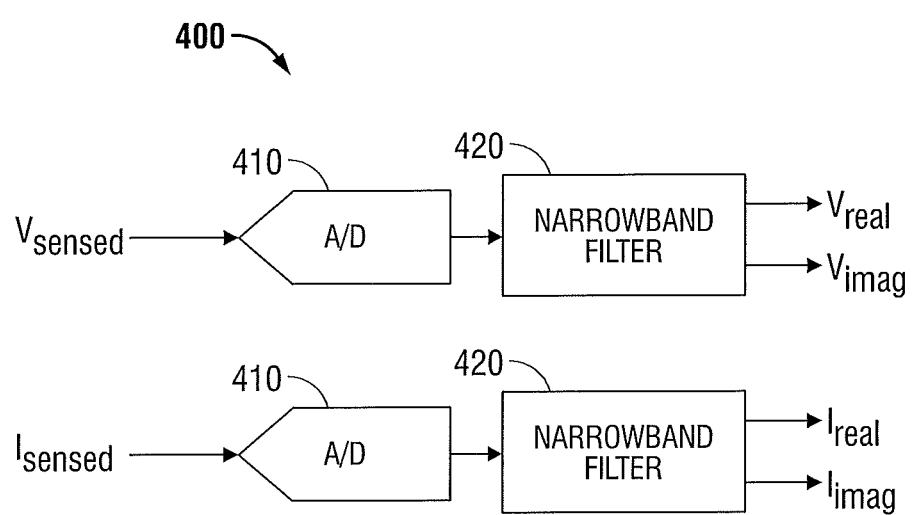
FIG. 4 is a block diagram of a measurement signal processing system, which includes narrowband filters, implemented by the generator circuitry of FIGS. 2A-2C in accordance with some embodiments of the present disclosure.

FIG. 4 is a block diagram of signal processing circuitry 400 for processing a voltage and a current output from the generator 110 to obtain a complex voltage and a complex current. The signal processing circuitry includes ADCs 410 and narrowband filters 420. The ADCs 410 convert the sensed voltage and current waveforms into digitized voltage and current waveforms, respectively, at a sampling frequency suitable for the electrosurgical generator 110. The narrowband filters 420 filter the digitized voltage and current waveforms to obtain a complex-valued voltage $V_{comp}$ and a complex-valued current $I_{comp}$, respectively. More specifically, the first narrowband filter 420 outputs two values: a real part $V_{real}$ and an imaginary part $V_{imag}$ of the complex-valued voltage $V_{comp}$. Likewise, the second narrowband filter 420 outputs two values: a real part $I_{comp}$ and an imaginary part $I_{imag}$ of the complex-valued current $I_{comp}$. The digital signal processor 314 of the controller 300 then calculates the real part of the impedance of the tissue using the complex-valued voltage $V_{comp}$ and the complex-valued current $I_{comp}$. The calculations for the real part of the impedance are derived from the following equations:

$$V_{comp} = V_{real} + jV_{imag} = a + jb, \qquad (1)$$

$$I_{comp} = I_{real} + j \cdot I_{imag} = c + j \cdot d, \qquad (2)$$

$$Z_{comp} = \frac{V_{comp}}{I_{comp}}, \text{ and} \qquad (3)$$

$$Z_{re} = \text{Real Part}(Z_{comp}) = \text{Real Part}\left(\frac{V_{comp}}{I_{comp}}\right), \qquad (4)$$

where $Z_{comp}$ is the complex impedance of the tissue and $Z_{real}$ is the real part of the complex impedance $Z_{comp}$. Substituting equations (1) and (2) into equation (3) results in the following equation:

$$Z_{comp} = \frac{V_{comp}}{I_{comp}} = \frac{a+jb}{c+jd} = \frac{ac+bd}{c^2+d^2} + j\frac{bc-ad}{c^2+d^2} = Z_{real} + jZ_{imag}. \qquad (5)$$

As shown in equation (5), the real part $Z_{real}$ of the complex impedance $Z_{comp}$ corresponds to $$\frac{ac+bd}{c^2+d^2}$$

and the imaginary part $Z_{imag}$ of the complex impedance $Z_{comp}$ corresponds to $$\frac{bc - ad}{c^2 + d^2}.$$

Thus, the real part $Z_{real}$ and the imaginary part $Z_{imag}$ of the complex impedance $Z_{comp}$ may be calculated by performing simple algebra on values output from the narrowband filters 420, i.e., by evaluating $$\frac{ac + bd}{c^2 + d^2},$$

rather than performing calculations on wideband RMS voltage and current values.

Although a wide-band real power estimate may be performed by a simple moving average filter of the sample-by-sample multiplication of voltage and current, for some sinusoidal waveforms a narrowband estimate may be sufficient. Similarly, the real part $P_{real}$ of the complex-valued power $P_{comp}$ may be calculated by performing simple algebra. The complex-valued power $P_{comp}$ may be expressed by the following equation:

$$P_{comp}=P_{real}+j\cdot P_{imag}=V_{comp}\cdot I_{comp}*=(a+j\cdot b)(c+j\cdot d)*= (ac+bd)+j(bc-ad),\qquad(6)$$

where $I_{comp}*$ is the complex conjugate of the complex current $I_{comp}$, which is $c-j\cdot d$. As shown in equation (6), the real part $P_{real}$ of the complex-valued power $P_{comp}$ corresponds to (ac+bd). Thus, the real part $P_{real}$ of the complex-valued power $P_{comp}$ may be calculated by simply evaluating the equation (ac+bd). The real part $P_{real}$ of the complex-valued power $P_{comp}$ may then be used to generate the control signal to the inner power control loop 274 by the DMAC 272.

The narrowband filters 420 may be implemented by a Goertzel Discrete Fourier Transform (DFT) algorithm. The Goertzel DFT algorithm may perform the following computations the outputs from voltage and performed according to the following equations:

$$x[n]=v(t_n)+\text{real}W\cdot x[n-1]-x[n-2],\text{ and}$$

$$y[n]=i(t_n)+\text{real}W\cdot y[n-1]-y[n-2],$$

for n=0 ... N-1, where N is the sample window size, $v(t_n)$ is the voltage sample at time $t_n$, $i(t_n)$ is the current sample at time $t_n$, and $$realW = 2\cdot\cos\left(2\cdot\pi\cdot\frac{10}{N}\right).$$

The real and imaginary parts of the complex-valued voltage and current may then be calculated according to the following equations:

$$a=0.5\cdot\text{real}W\cdot x[n-1]-x[n-2],$$

$$b=\text{imag}W\cdot x[n-1],$$

$$c=0.5\cdot\text{real}W\cdot y[n-1]-y[n-2],\text{ and}$$

$$d=\text{imag}W\cdot x[n-1],$$

where $$imagW = \sin\left(2\cdot\pi\cdot\frac{10}{N}\right),$$

a is the real part of the complex-valued voltage, b is the imaginary part of the complex-valued voltage, c is the real part of the complex-valued current, and d is the imaginary part of the complex-valued current.

Figure 5A:
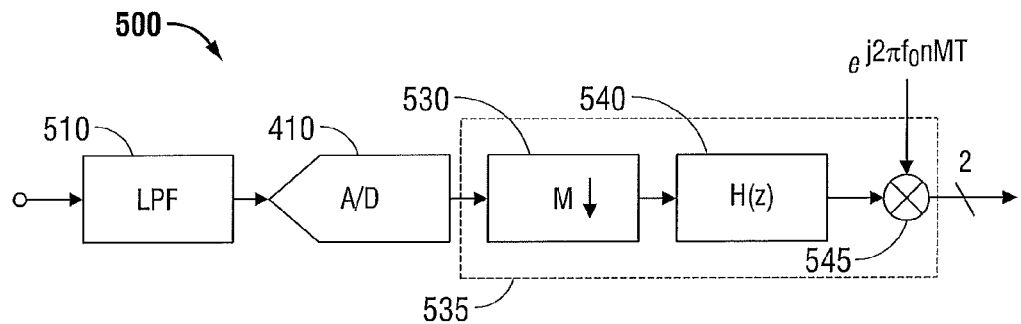
FIGS. 5A and 5B are block diagrams of measurement signal processing systems, which include narrowband filters, implemented by the generator circuitry of FIGS. 2A-2C in accordance with further embodiments of the present disclosure.

FIG. 5A is a block diagram of an alternative narrowband measurement signal processing circuit 500 according to a further embodiment of the present disclosure. The measurement signal processing system 500 includes a low pass filter (LPF) 510, an ADC 410, a decimator 530, a prototype filter 540, e.g., a lowpass filter, with impulse response H(z), and a heterodyne mixer 545. The decimator 530, polyphase filter 540, and heterodyne mixer 545 form a filter structure known as a polyphase filter with heterodyne. As with the measurement signal processing system of FIG. 4, the measurement signal processing system 500 determines the real and imaginary parts of a signal, e.g., a voltage or current signal sensed by the sensors 240 at the output of the generator 110, input to the measurement signal processing system 500.

In operation, the input signal passes through the LPF 510, which removes unwanted noise from the input signal. The ADC 410 samples the filtered voltage or current at a suitable sampling frequency, which may be an integer multiple of the frequency of the input signal 410. Then, the polyphase filter 535 downsamples and filters the sampled input signal using the commutated phases of the prototype filter 540 described in more detail below with reference to FIGS. 7, 8, and 9.

The heterodyne mixer 545 multiplies the filtered input signal with a carrier signal that has a frequency of $f_0$ nMT, where $f_0$ is the center frequency of the polyphase filter 540, M is the number of phases in the polyphase filter 540, n is an index of the sampled input signal, and T is a phase index ranging from 0 to (L−1). Thus, when a frequency of the of the input signal is the same as the frequency of the carrier signal $f_0$, the heterodyne polyphase filter 500 outputs the narrowband real and imaginary parts of the filtered input signal described in further detail below with reference to FIGS. 7, 8, and 9.

Figure 5B:
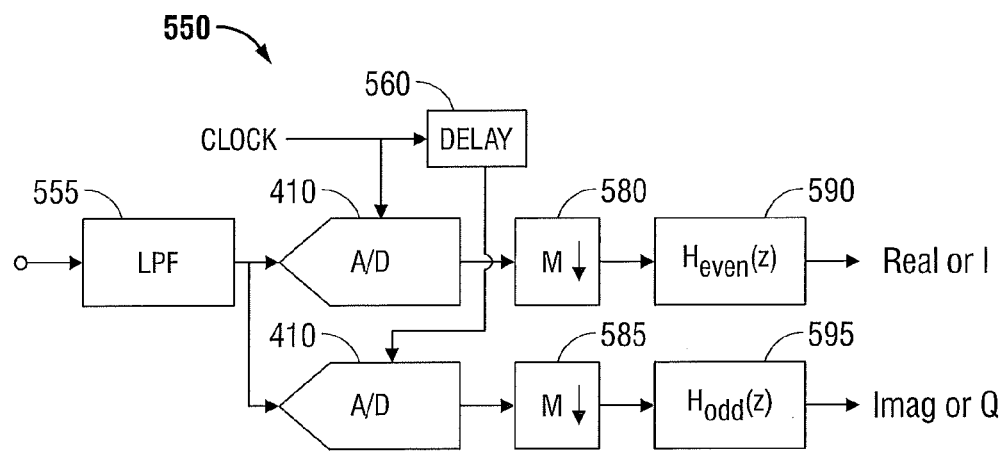

FIG. 5B is a block diagram illustrating a measurement signal processing system 550 according to yet another embodiment of the present disclosure. The measurement signal processing system 550 employs a quadrature structure to obtain the real or in-phase (I) component of an input signal and the imaginary or quadrature (Q) component of the input signal. As described above with reference to FIG. 5A, the input signal passes through the LPF 555 to remove unwanted noise.

The ADCs 410 sample the filtered input signal at a suitable sampling frequency set by the clock, which provides a clock signal to the ADCs 410. The clock signal provided to ADC 410 is delayed by delay block 560 to shift the phase of the filtered input signal in the frequency domain in order to obtain the imaginary or quadrature component of the filtered input signal. The samples obtained by the ADCs 410 are then downsampled by polyphase filter structures including decimators 580 and 585 and prototype filters 590 and 595. The polyphase filters efficiently narrowband filter the downsampled signals to obtain the real or in-phase (I) component and the imaginary or quadrature (Q) component of the input signal.

Figure 6A:
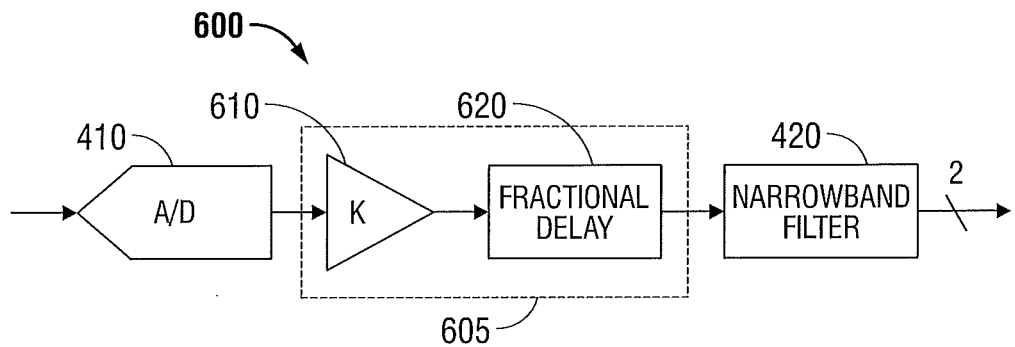
FIGS. 6A and 6B are block diagrams of measurement signal processing systems, which include narrowband filters, implemented by the generator circuitry of FIGS. 2A-2C in accordance with still further embodiments of the present disclosure.

The measurement signal processing systems 500 and 550 of FIGS. 5A and 5B may further include a compensator to improve the accuracy of the measurements of the real and imaginary parts of the voltage and current. FIG. 6A is a block diagram of a measurement signal processing system 600 that includes a compensator 605 for correcting the magnitude and phase of the input signal provided to the narrowband filter 420 of FIG. 4.

The compensator 605 includes a gain 610 and a fractional delay line 620 that are coupled to each other. The gain 610 increases the magnitude of the input signal at a single frequency based on the value of a gain correction factor K, which may be determined through a calibration procedure. The calibration procedure may involve adjusting the gain correction factor K until the magnitude of the output from the compensator reaches a desired level.

Fractional delay line 620 adjusts the phase of the input signal at a single frequency based on the value of a time-delay correction factor. The fractional delay line 620 may be expressed as $z^{-\Delta t_{CF}}$, where $\Delta t_{CF}$ is the time-delay correction factor. The time delay correction factor $\Delta t_{CF}$ may also be determined through a calibration procedure.

Figure 6B:
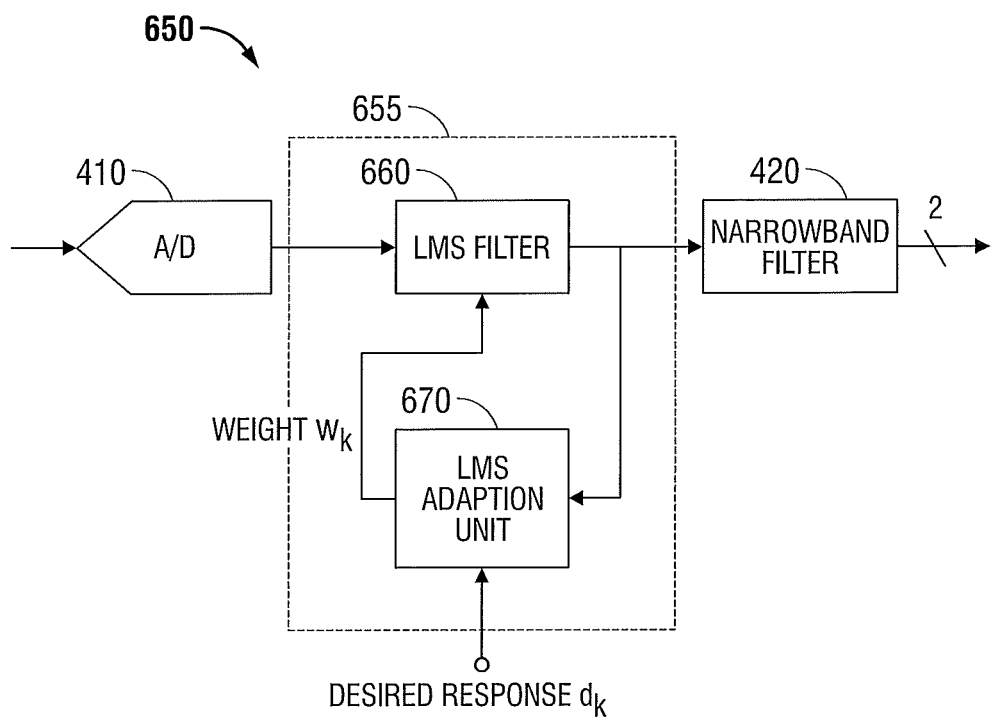

FIG. 6B is a block diagram of a measurement signal processing system 650 according to still further embodiments of the present disclosure. The measurement signal processing system 650 includes the ADC 410 and polyphase filter 420 of FIG. 4 and a compensator 655 coupled between the ADC 410 and the polyphase filter 420. The compensator 655 employs a least mean square (LMS) filter 660 and an LMS adaptation unit 670. The LMS filter 660 filters an input waveform (e.g., the digitized voltage or current waveform) based on a weight vector $w_k$ to produce a filtered output waveform. The weight vector $w_k$ is produced by the LMS adaptation unit 670 and may be a pre-computed "pseudo-filter" or time sequence. The desired response $d_k$ may have an idealized magnitude and phase versus frequency response of a converged adaptive filter in an electrosurgical system. For instance, if the converged output current from the system matches the pre-measured magnitude and phase values at one or more frequencies, then this information is used to construct a desired response sequence $d_k$ and/or a pseudo-filter.

The desired response sequence $d_k$ is formed by sampling a sinusoidal calibration waveform d(t) having a known amplitude of excitation or the same amplitude as the test waveform x(t) (i.e., $A_1$), but delayed according to a measured or known phase $\theta_1$ between the input of the ADC 410 and the output of the narrowband filter 420. In other words, the phase $\theta_1$ represents the delays introduced by the ADC 410 and other electronic or digital components disposed between the RF amplifier 230 shown in FIG. 2 and the output of the narrowband filter 420. The sinusoidal calibration waveform may be expressed as follows:

$$d(t)=A_1 \sin(2\pi f_1 t+\theta_1).$$

For multiple frequencies $f_n$, the calibration procedure involves using the RF amplifier 230 to generate the following series of test waveforms:

$$x_n(t)=A_n \sin(2\pi f_n t),$$

where n=1, . . . , N and the amplitudes $A_n$ are measured or known values. The series of test waveforms are summed together and applied to a test resistive load.

The desired response sequence $d_k$ for multiple frequencies is formed by sampling the sum of multiple sinusoidal calibration waveforms given by the expression:

$$d_n(t)=A_n \sin(2\pi f_n t+\theta_n).$$

The calibration waveforms $d_n(t)$ have known amplitudes of excitation or the same amplitudes as the respective test waveforms $x_n(t)$ (i.e., $A_n$), but are delayed according to measured or known phases $\theta_n$ between the input of the ADC 410 and the output of the polyphase filter 420.

At the end of the adaptation process, the estimated phases of the voltage and current waveforms will be equal to or approximately equal to each other at desired frequencies of interest. Also, the magnitudes of the measured voltage and current will be identical to or approximately identical to the respective magnitudes of the estimated voltage and current.

Figure 7:
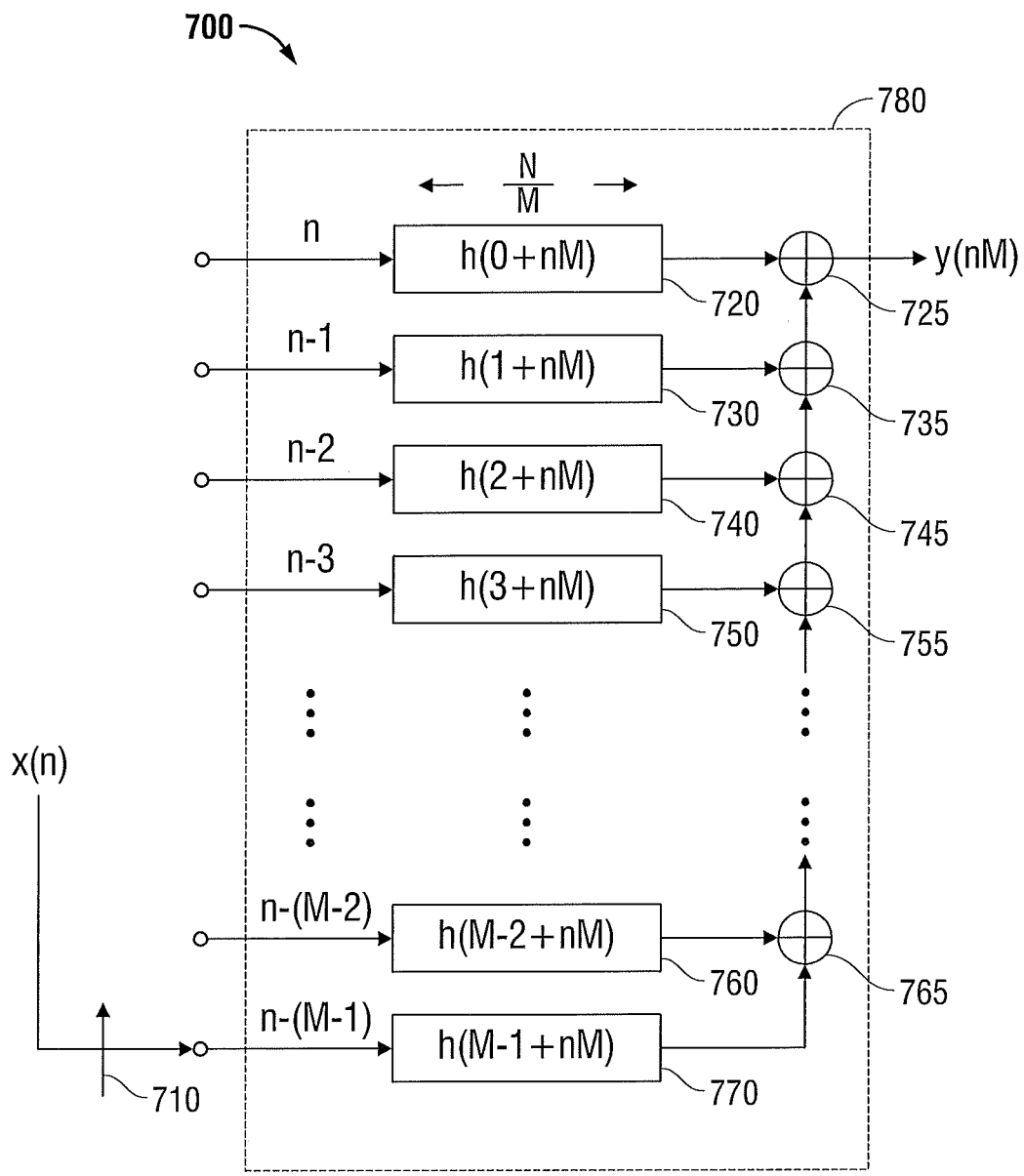
FIG. 7 is a block diagram of a polyphase filter in accordance with some embodiments of the present disclosure.

FIG. 7 is a block diagram of a baseband polyphase filter 700 that may be used to implement the narrowband filters 420, 540, 590, and 595 of FIGS. 4-6. The baseband polyphase filter 700 includes M subfilters 720, 730, 740, 750, 760, and 770, and (M−1) adders 725, 735, 745, 755, and 765. The baseband polyphase filter 700 further includes a commutating switch 710 that delivers different phases of the input data to each of the subfilter 720, 730, 740, 750, 760, and 770. More specifically, the switch 710 delivers input data x[0], x[M], . . . , x[(L−1)M] to the first subfilter 820; delivers input data x[1], x[1+M], . . . , x[1+(L−1)M] to the second subfilter 730; . . . ; and delivers input data x[M−1], x[M−1+M], . . . , and x[M−1+(L−1)M] to the last subfilter 770. In this manner, each subfilter receives and filters L samples (i.e., N/M) of input data in parallel. Adder 765 adds filtered outputs from subfilters 770 and 760; adder 755 adds filtered output from phase 750 and the sum of output from lower phases; . . . ; and adder 725 adds all outputs from the M subfilters 720, 730, 740, 750, 760, and 770. The result of the addition is the output y(nM).

As shown in FIG. 8, the output y(nM) is generated every M samples of the input data. Thus, the polyphase filter 800 has an inherent delay of M input data samples. The value for M may be chosen to be synchronized with an RF frequency for electrosurgery and a sampling frequency of the ADCs to provide real-time electrosurgical operation.

Figure 8A:
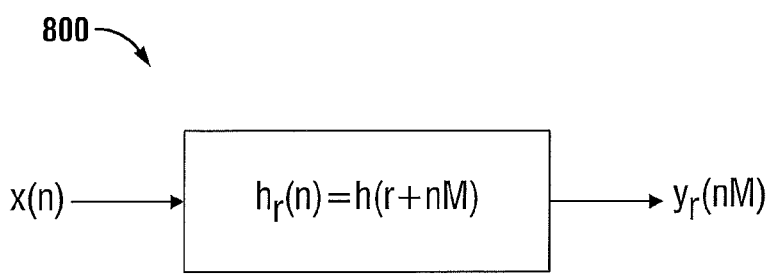
FIGS. 8A and 8B are block diagrams of the $r^{th}$-subfilter of the polyphase filter of FIG. 7.

FIG. 8A is a block diagram of an $r^{th}$ subfilter 800 of the polyphase filter 700 of FIG. 7. As described above, the polyphase filter 700 includes multiple subfilters that filter different phases of the input data. The polyphase filter 700 combines the output from each of the r subfilters to generate a complex-valued output. Each subfilter 800 of the polyphase filter 700 may be a finite impulse response (FIR) filter. Since the polyphase filter 700 performs a series of small filter calculations for each phase of the input data in parallel, computational efficiency is greatly increased. Generally, the number of data samples (L) is an integer multiple of the number of phases (M) of the polyphase filter 800. FIG. 7A specifically shows the $r^{th}$-phase 710 that receives input x(n), i.e., the sensed voltage or current, and outputs $y_r(nM)$, i.e., the real and imaginary parts of the sensed voltage or current.

Figure 8B:
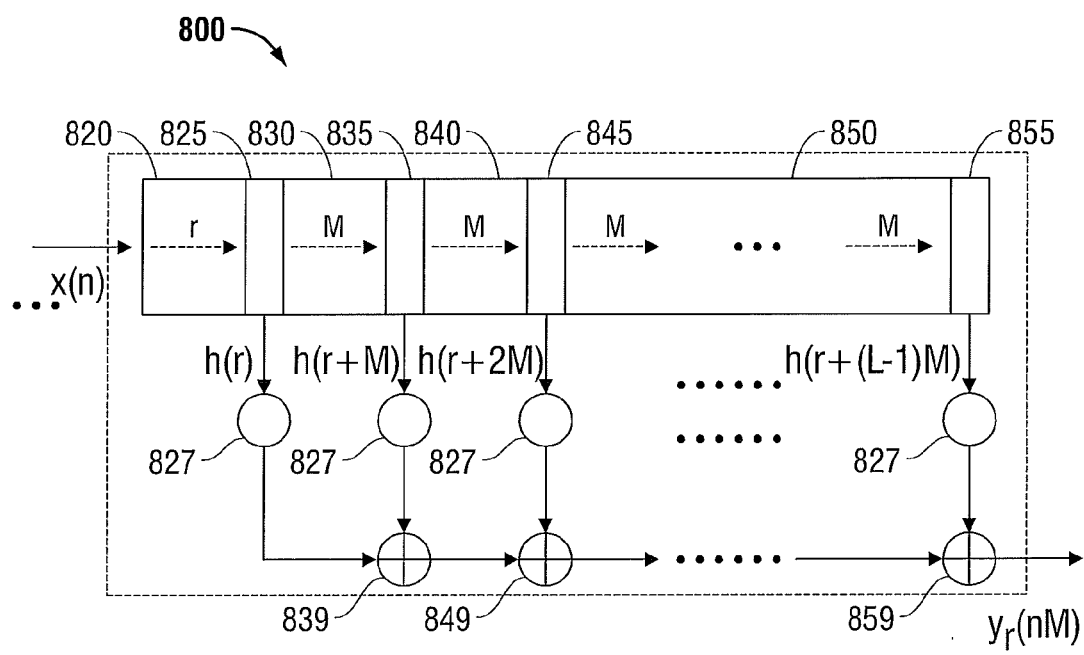

FIG. 8B illustrates the structure of the $r^{th}$-subfilter 800 of the polyphase filter 700 of FIG. 7. The $r^{th}$-subfilter 800 includes a plurality of adders 839, 849, and 859, and a filter 827. The $r^{th}$-subfilter 800 receives a series of input data 820, 825, 830, 835, 845, 850, and 855, which are digitized values of a sensed voltage or current. In the $r^{th}$-subfilter 800, the $r^{th}$-data 825 is filtered by the filter 827 to obtain h(r), the $(r+M)^{th}$ input data is filtered by the filter 827 to obtain h(r+M), and the first adder 839 adds h(r) and h(r+M); the $(r+2M)^{th}$-data is filtered by the filter 827 to obtain h(r+2M) and the second adder 849 adds h(r+2M) and the sum of h(r) and h(r+M); . . . and, lastly, the $(r+(L-1)M)^{th}$ data is filtered by the filter 827 to obtain h(r+(L−1)M), and the $(L-1)^{th}$ adder 859 adds h(r+(L−1)M) and the sum of h(r), h(r+M), h(r+2M), . . . , and h(r+(L−2)M) to produce $y_r(nM)$. The $r^{th}$-subfilter processes L samples of the input data. In this manner, the computational efficiency for N samples of input data is reduced by a factor of M, which is the number of subfilters in the polyphase filter 700.

Figure 9:
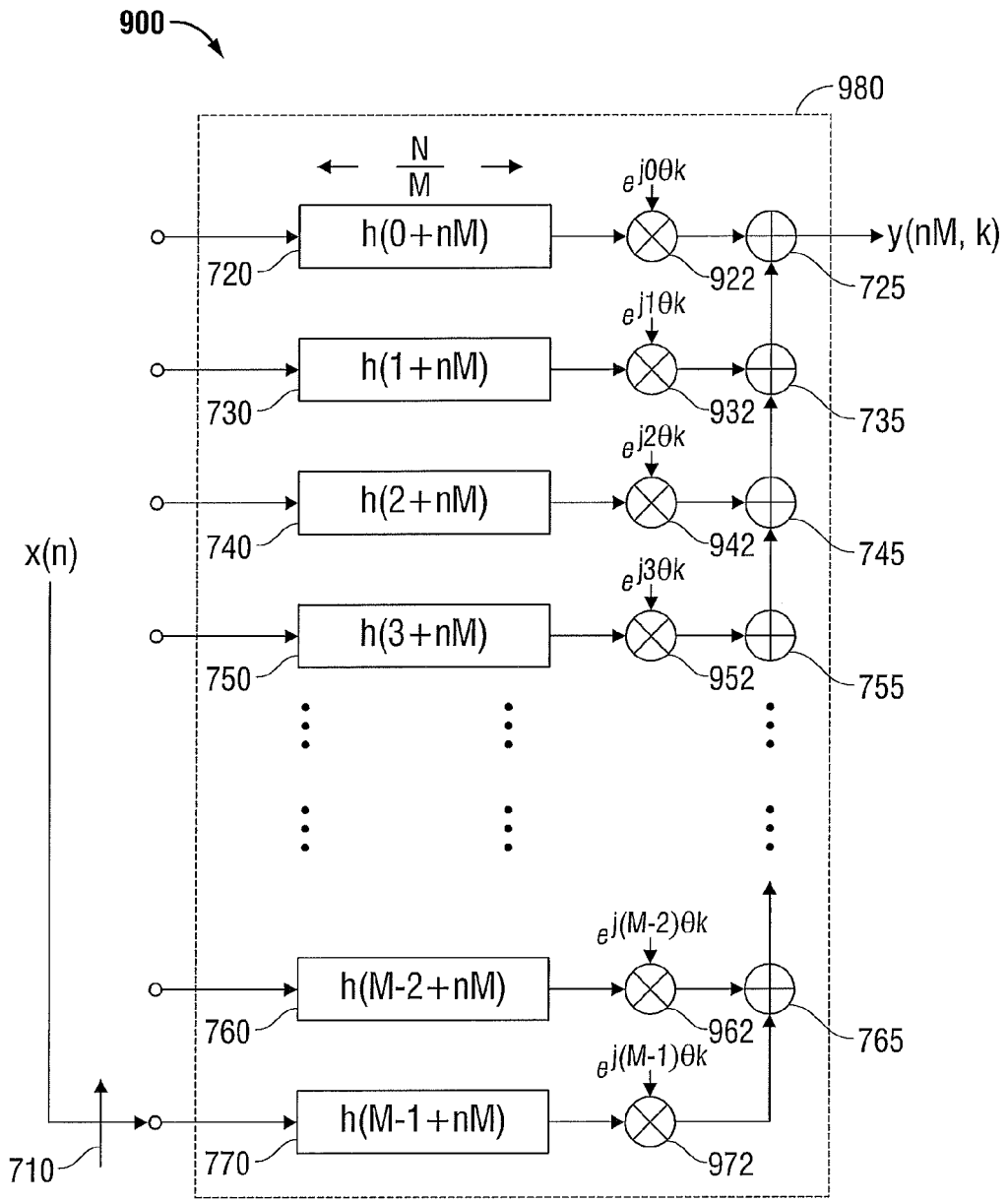
FIG. 9 is a block diagram of a carrier-centered polyphase filter in accordance with other embodiments of the present disclosure.

FIG. 9 is a block diagram of a heterodyne polyphase filter 900 that may be used to implement the narrowband filters 420, 540, 590, 595 of FIGS. 4-6. Typically, the heterodyne technique mixes or multiplies two waveforms whose frequencies are $f_1$ and $f_2$, and produces a waveform that has frequencies of the sum $(f_1+f_2)$ and difference $(f_1-f_2)$ of the frequencies $f_1$ and $f_2$. These two new frequencies are called heterodynes. The following equation illustrates the result of the heterodyne technique applied to two sinusoids:

$$\sin(2\pi f_1 t)\sin(2\pi f_2 t) = \frac{1}{2}\cos(2\pi(f_1-f_2)t) - \frac{1}{2}\cos(2\pi(f_1+f_2)t).$$

The carrier-centered polyphase filter 900 employs the heterodyne technique. The carrier-centered polyphase filter 900 includes the switch 710, the M subfilters 720, 730, 740, 750, 760, and 770, and the adders 725, 735, 745, 755, and 765 of FIG. 7, and carrier-signal multipliers 922, 932, 942, 952, 962, and 972. The center frequency of the carrier-centered polyphase filter 900 is a harmonic multiple of a sampling frequency of the plurality of the ADCs and a harmonic multiple of a frequency of the electrosurgical energy. Outputs from each subfilter 720, 730, 740, 750, 760, and 770 are multiplied by a respective carrier signal using a respective multiplier 922, 932, 942, 952, 962, and 972, the results of which are added together by adders 924, 934, 944, 954, and 964 to obtain a final output y(nM, k).

The carrier signals 922, 932, 942, 952, 962, and 972 are in the form of an exponential $e^{jr\theta k}$, where $\theta$ is $$\frac{2\pi}{M}$$

and r is 0, 1, 2, . . . , M−1. A single period of the $e^{jr\theta k}$ is harmonically related to M, which is the number of subfilters of the carrier-centered polyphase filter 900. The first index nM of the final output y(nM, k) is the time index and the second index k is the frequency index.

In further embodiments, the subfilters 720, 730, 740, 750, 760, and 770 and respective multipliers 922, 932, 942, 952, 962, and 972 may be merged into a Hilbert filter to further enhance calculation efficiency without loss of accuracy.

In still further embodiments, the narrowband filters 420, 540, 590, and 595 of FIGS. 4-6 may be implemented by a single-frequency discrete Fourier transform, such as the Goertzel filter described above.

Figure 10:
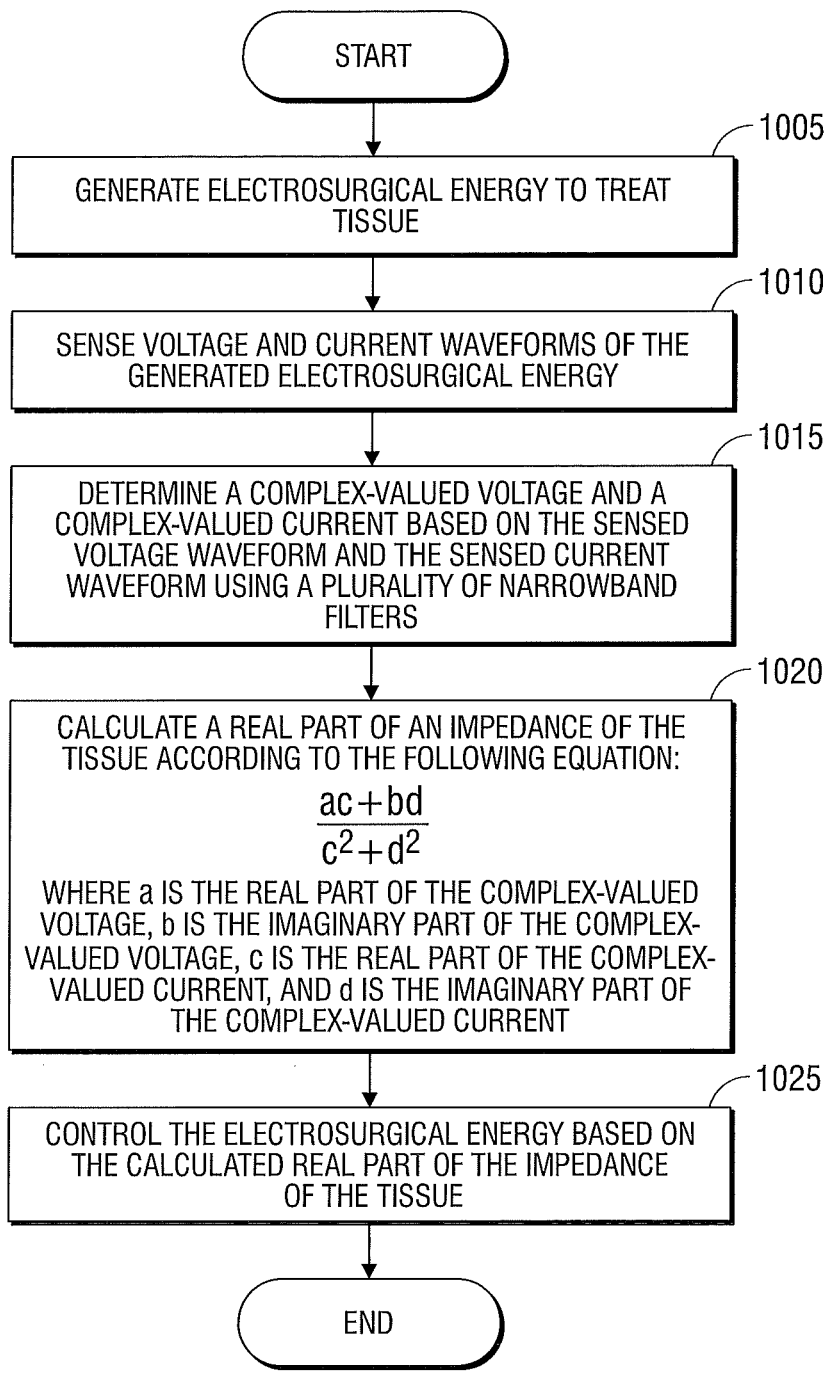
FIG. 10 is a flow diagram of a method for an electrosurgical generator for determining a real part of tissue impedance in accordance with embodiments of the present disclosure.

FIG. 10 is a flow diagram of a method for an electrosurgical generator for determining a real part of tissue impedance in accordance with embodiments of the present disclosure. In step 1005, electrosurgical energy for treating tissue is generated. In step 1010, voltage and current waveforms of the generated electrosurgical energy are sensed. In step 1015, complex-valued voltage and current are determined based on the sensed voltage and current waveforms using a plurality of narrowband filters. In step 1020, the real part of the tissue impedance is calculated according to the following equation:

$$\frac{ac+bd}{c^2+d^2},$$

where a is the real part of the complex-valued voltage, b is the imaginary part of the complex-valued voltage, c is the real part of the complex-valued current, and d is the imaginary part of the complex-valued current. Then, in step 1025, the electrosurgical energy is controlled based on the calculated real part of the tissue impedance.

Figure 11:
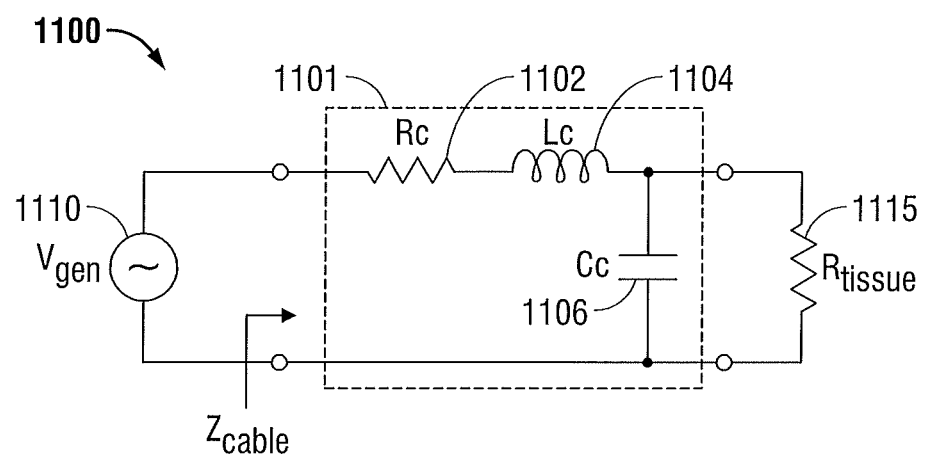
FIG. 11 is a simplified circuit diagram of an electrosurgical generator circuit including a lumped cable model.

In some embodiments, where the imaginary impedance component cannot be neglected with respect to the overall magnitude, compensation for more accurate calculation of the load tissue resistance 1115 may be necessary. Typically, the cable and electrosurgical instrument interposed between the generator and the tissue have parasitic values that, at low RF frequencies (e.g., frequencies<<10 MHz), may be modeled as lumped values (as opposed to more complicated two-port or transmission-line models) of series inductance and resistance with terminating shunt capacitance across the tissue load resistance. Such a model is shown in FIG. 11 as a lumped cable model 1101, which forms a part of a electrosurgical system circuit 1100. The lumped cable model 1101 includes a resistance 1102 and an inductance 1104 in series with a generator 1110, and a capacitance 1106 in parallel with the generator 1110.

Often, the tissue resistance load 1115 is much greater than the series component magnitude and much less than the shunt component magnitudes. For these cases, the real impedance component may be sufficient for estimating the tissue resistance 1115 as described above. However, if the tissue resistance 1115 becomes very small, which occurs sometimes as moist tissue is heated and the ions become more mobile, or if the tissue resistance 1115 becomes very large, which occurs sometimes when most of the tissue moisture is driven away and the current-flow paths become tortuous, compensation may be made for either the series components, i.e., the resistance 1102 and the inductance 1104, or the shunt components, i.e., the capacitance 1106, as long as they are known a priori. If the cable resistance 1102, inductance 1104, and capacitance 1106 are known, then the estimates for tissue resistance 1115 and real power dissipation in the tissue are derived from the following cases:

Case 1: If $$\|R_c + j\omega_0 L_c\| << R_{tissue} << \left\|\frac{1}{j\omega_0 C_c}\right\|$$

(where "<<" means "at least an order of magnitude or more"), then $Z_{real}=\text{Re}\{\vec{Z}_{cable}\}\cong\hat{R}_{tissue}$ and $P_{real}=\text{Re}\{\vec{P}_{cable}\}\cong\hat{P}_{avg}$ ("^" means "an estimate of").

Case 2: If $$\|R_c + j\omega_0 L_c\| << R_{tissue} \rightarrow \left\|\frac{1}{j\omega_0 C_c}\right\|$$

(where "→" means "approaching within an order of magnitude"), then $$R_{tissue} \cong \frac{1 \pm \sqrt{1 - 4\cdot Z_{real}^2 \cdot \omega_0^2 \cdot C_c^2}}{2\cdot\omega_0^2\cdot C_c^2\cdot Z_{real}}$$

and $\hat{P}_{avg}\cong\text{Re}\{\vec{P}_{cable}\}=P_{real}$.

Case 3: If $$\|R_c + j\omega_0 L_c\| \leftarrow R_{tissue} << \left\|\frac{1}{j\omega_0 C_c}\right\|,$$

then $R_{tissue} \cong (Z_{real} - R_c) = \text{Re}\{\vec{Z}_{cable}\} - R_c$ and $$\hat{P}_{avg} \cong \text{Re}\{\vec{P}_{cable}\} \cdot \left(1 - \frac{R_c}{Z_{real}}\right) = P_{real}\left(1 - \frac{R_c}{Z_{real}}\right).$$

Case 4: If $R_{tissue} \ll \|R_c + j\omega_0 L_c\|$ and $R_c \ll \omega_0 L_c$, then assume there is a short circuit when the magnitude of $\vec{Z}_{cable} \leq \omega_0 L_c$ or $Z_{real} \to R_c$.

Case 5: If $$R_{tissue} \gg \left\|\frac{1}{j\omega_0 C_c}\right\|,$$

then assume there is an open circuit when the magnitude of $$\vec{Z}_{cable} \cong \frac{1}{\omega_0 C_c}$$

or as $Z_{real} \to 0$.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An electrosurgical generator comprising:
   an output stage configured to generate electrosurgical energy to treat tissue;
   a plurality of sensors configured to sense a voltage waveform and a current waveform of the electrosurgical energy; and
   a controller coupled to the output stage and the plurality of sensors and configured to control the generated electrosurgical energy, the controller comprising:
   a signal processor configured to (1) determine a complex-valued voltage and a complex-valued current based on the voltage waveform and the current waveform sensed by the plurality of sensors using a plurality of narrowband filters, and (2) calculate a real part of an impedance of the tissue using the complex-valued voltage and the complex-valued current; and
   an output controller configured to control the output stage based on the calculated real part of the impedance of the tissue,
   wherein the signal processor calculates the real part of the tissue impedance according to the following equation:

$$\frac{ac + bd}{c^2 + d^2},$$

where a is the real part of the complex-valued voltage, b is the imaginary part of the complex-valued voltage, c is the real part of the complex-valued current, and d is the imaginary part of the complex-valued current.

2. The electrosurgical generator according to claim 1, wherein the plurality of narrowband filters are polyphase decimator filters or Goertzel DFT filters.

3. The electrosurgical generator according to claim 1, wherein the plurality of narrowband filters are heterodyne, carrier-centered polyphase decimator filters having a center frequency that is a harmonic multiple of a frequency of the electrosurgical energy.

4. The electrosurgical generator according to claim 1, wherein the electrosurgical energy is Radio Frequency (RF) energy.

5. The electrosurgical generator according to claim 1, wherein the signal processor calculates the imaginary part of the tissue impedance according to the following equation:

$$\frac{bc - ad}{c^2 + d^2},$$

where a is the real part of the complex-valued voltage, b is the imaginary part of the complex-valued voltage, c is the real part of the complex-valued current, and d is the imaginary part of the complex-valued current.

6. The electrosurgical generator according to claim 1, wherein the signal processor calculates the magnitude of the tissue impedance based on the calculated real and imaginary parts of the tissue impedance.

7. The electrosurgical generator according to claim 1, further comprising:
   a plurality of analog-to-digital converters (ADCs) configured to sample the sensed voltage waveform and the sensed current waveform to obtain a predetermined number of samples of each of the sensed voltage waveform and the sensed current waveform,
   wherein the predetermined number of samples corresponds to an integer number of periods of the voltage waveform and the current waveform.

8. The electrosurgical generator according to claim 7, further comprising:
   a plurality of low pass filters configured to filter the sensed voltage waveform and the sensed current waveform before the plurality of ADCs sample the sensed voltage waveform and the sensed current waveform.

9. The electrosurgical generator according to claim 8, further comprising:
   a plurality of decimators configured to decimate the sampled voltage waveform and the sampled current waveform before the plurality of narrowb and filters filter the decimated voltage waveform and the decimated current waveform.

10. The electrosurgical generator according to claim 1, wherein the output controller generates a feedback waveform based on a difference between the real part of the impedance and a desired real part of the impedance, and
    wherein the feedback waveform is used to control the output stage.

11. The electrosurgical generator according to claim 1, wherein the controller is selected from the group consisting of a field programmable gate array, an application specific integrated circuit, a digital signal processor, a programmable digital signal processor, an application specific standard product integrated circuit, and combinations thereof.

12. A method for an electrosurgical generator, the method comprising:
    generating electrosurgical energy to treat tissue;
    sensing a voltage waveform and a current waveform of the generated electrosurgical energy;

determining a complex-valued voltage and a complex-valued current based on the sensed voltage waveform and the sensed current waveform using a plurality of narrowband filters;
calculating a real part of an impedance of the tissue; and
controlling the electrosurgical energy based on the calculated real part of the impedance of the tissue,
wherein the real part of the tissue impedance is calculated according to the following equation:

$$\frac{ac+bd}{c^2+d^2},$$

where a is the real part of the complex-valued voltage, b is the imaginary part of the complex-valued voltage, c is the real part of the complex-valued current, and d is the imaginary part of the complex-valued current.

13. The method according to claim 12, wherein the plurality of narrowband filters are polyphase decimator filters or Goertzel DFT filters.

14. The method according to claim 12, wherein the plurality of narrowband filters are heterodyne, carrier-centered polyphase decimator filters having a center frequency that is a harmonic multiple of a frequency of the electrosurgical energy.

15. The method according to claim 12, further comprising calculating the imaginary part of the tissue impedance according to the following equation:

$$\frac{bc-ad}{c^2+d^2},$$

where a is the real part of the complex-valued voltage, b is the imaginary part of the complex-valued voltage, c is the real part of the complex-valued current, and d is the imaginary part of the complex-valued current.

16. The method according to claim 15, further comprising calculating the magnitude of the tissue impedance based on the calculated real and imaginary parts of the tissue impedance.

17. The method according to claim 12, further comprising:
sampling the sensed voltage waveform and the sensed current waveform to obtain a predetermined number of samples of each of the sensed voltage waveform and the sensed current waveform,
wherein the predetermined number of samples corresponds to an integer number of periods of the voltage waveform and the current waveform.

18. A non-transitory storage medium storing instructions that, when executed by a processor, performs a method for controlling an electrosurgical generator, the method comprising:
generating electrosurgical energy to treat tissue;
sensing a voltage waveform and a current waveform of the generated electrosurgical energy;
determining a complex-valued voltage and a complex-valued current based on the sensed voltage waveform and the sensed current waveform using a plurality of narrowband filters;
calculating a real part of an impedance of the tissue; and
controlling the electrosurgical energy based on the calculated real part of the impedance of the tissue,
wherein the real part of the tissue impedance is calculated according to the following equation:

$$\frac{ac+bd}{c^2+d^2},$$

where a is the real part of the complex-valued voltage, b is the imaginary part of the complex-valued voltage, c is the real part of the complex-valued current, and d is the imaginary part of the complex-valued current.

19. The non-transitory storage medium according to claim 18, wherein the processor is selected from the group consisting of a field programmable gate array, an application specific integrated circuit, a digital signal processor, a programmable digital signal processor, an application specific standard product integrated circuit, and combinations thereof.

* * * * *